United States Patent
Edelman et al.

(10) Patent No.: US 10,526,457 B2
(45) Date of Patent: Jan. 7, 2020

(54) NARROWLY DISTRIBUTED MULTI-ARMED POLYETHYLENE GLYCOL COMPOUNDS, HYDROGELS, AND METHODS

(71) Applicants: Massachusetts Institute of Technology, Cambridge, MA (US); NOF Corporation, Tokyo (JP)

(72) Inventors: Elazer Edelman, Brookline, MA (US); Natalie Artzi, Brookline, MA (US); Hyun Seok Song, Belmont, MA (US); Yuji Yamamoto, Kanagawa (JP); Hiroki Yoshioka, Kanagawa (JP); Ken-ichiro Nakamoto, Kanagawa (JP)

(73) Assignees: NOF Corporation, Kanagawa (JP); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/764,942

(22) PCT Filed: Sep. 30, 2016

(86) PCT No.: PCT/US2016/054718
§ 371 (c)(1),
(2) Date: Mar. 30, 2018

(87) PCT Pub. No.: WO2017/059220
PCT Pub. Date: Apr. 6, 2017

(65) Prior Publication Data
US 2018/0282495 A1 Oct. 4, 2018

Related U.S. Application Data

(60) Provisional application No. 62/235,026, filed on Sep. 30, 2015.

(51) Int. Cl.
| | | |
|---|---|---|
| *A61L 27/18* | (2006.01) | |
| *A61L 27/38* | (2006.01) | |
| *A61L 27/52* | (2006.01) | |
| *A61L 27/54* | (2006.01) | |
| *C08J 3/24* | (2006.01) | |
| *A61K 9/00* | (2006.01) | |
| *A61L 27/20* | (2006.01) | |

(52) U.S. Cl.
CPC ............. *C08J 3/246* (2013.01); *A61K 9/0024* (2013.01); *A61L 27/18* (2013.01); *A61L 27/20* (2013.01); *A61L 27/38* (2013.01); *A61L 27/3834* (2013.01); *A61L 27/52* (2013.01); *A61L 27/54* (2013.01); *A61L 2400/06* (2013.01); *C08J 2305/02* (2013.01); *C08J 2343/02* (2013.01); *C08J 2371/02* (2013.01)

(58) Field of Classification Search
None
See application file for complete search history.

(56) References Cited

U.S. PATENT DOCUMENTS

| | | | |
|---|---|---|---|
| 2006/0078536 A1* | 4/2006 | Kodokian | A61K 31/785 424/78.27 |
| 2010/0015231 A1* | 1/2010 | Lu | A61K 9/0024 424/488 |
| 2010/0255101 A1* | 10/2010 | Lu | A61L 24/0031 424/488 |
| 2012/0014909 A1* | 1/2012 | Chenault | A61L 24/0031 424/78.37 |
| 2012/0148523 A1* | 6/2012 | Lu | A61L 26/0023 424/78.38 |
| 2015/0174156 A1 | 6/2015 | Artzi et al. | |
| 2017/0106117 A1 | 4/2017 | Artzi et al. | |
| 2017/0333304 A1 | 11/2017 | Artzi et al. | |

FOREIGN PATENT DOCUMENTS

| | | | | |
|---|---|---|---|---|
| WO | 2015/017340 A2 | | 2/2015 | |
| WO | WO 2015/017340 | * | 2/2015 | ............. A61K 31/77 |
| WO | WO-2015017340 A2 | * | 2/2015 | ............ A61L 24/043 |

OTHER PUBLICATIONS

PCT International Search Report and Written Opinion for PCT Application No. PCT/US2016/054718 dated Jan. 2, 2017 (9 pages).

* cited by examiner

*Primary Examiner* — Brian Gulledge
(74) *Attorney, Agent, or Firm* — Eversheds Sutherland (US) LLP

(57) ABSTRACT

Provided herein are narrowly distributed multi-armed polyethylene glycol compounds, and hydrogels containing the same. Also provided are methods for treating, adhering, or sealing a biological tissue with hydrogels, and kits for making a hydrogel. Drug releasing compositions also are provided that include a narrowly distributed multi-armed polyethylene glycol compound.

32 Claims, 6 Drawing Sheets

NARROWLY DISTRIBUTED MULTI-ARMED POLYETHYLENE GLYCOL COMPOUNDS, HYDROGELS, AND METHODS

CROSS-REFERENCE TO RELATED APPLICATION

This application is a U.S. national stage application of PCT/US2016/054718, filed Sep. 30, 2016, which claims priority to U.S. Provisional Patent Application No. 62/235,026, filed Sep. 30, 2015. The contents of these applications are incorporated herein by reference.

BACKGROUND

Hydrogels, primarily due to their relatively high water content, have been used in tissue engineering and drug delivery, and can allow for nearly free diffusion of drugs and/or nutrients. Regarding their water content, hydrogels can contain up to 60-70% by weight of water. Hydrogels can be modified readily with a range of chemical functionalities, which may impart at least one of bioactivity, controlled degradability, and a variety of pore sizes.

Hydrogels also can be advantageous due to their ability to be injected in a fluid state, conform to the shape of a tissue, and/or be solidified in situ using a variety of chemical and physical crosslinking methodologies. The crosslinking methods often can be extended to create hydrogels that are cohesive and capable of adhering to a surrounding tissue, thereby possibly enhancing tissue-biomaterial integration.

Hydrogels, however, generally have weak mechanical properties, e.g., modulus, toughness, and/or strength, compared to many biological tissues. Most hydrogels are quite brittle and weak. As a result, hydrogels frequently are applied only to softer tissues. Also, some injected hydrogels flow too readily prior to gelation, thereby complicating their implantation in wet conditions and/or in difficult geometries.

There exists a need for hydrogels that have mechanical properties that permit their use with a number of different tissues in a variety of locations.

BRIEF SUMMARY

Provided herein are kits for making a hydrogel. In embodiments, the kits comprise a first part that includes a first solution comprising an aldehyde component comprising at least one of (i) a first polymer component comprising a first polymer having one or more aldehydes, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol; and a second part that includes a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol.

Also provided are drug delivery compositions. In embodiments, the drug delivery compositions comprise a first solution comprising an aldehyde component comprising at least one of (i) a first polymer component comprising a first polymer having one or more aldehydes, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol; a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol; and a drug dispersed within the first solution, the second solution, or both the first solution and the second solution.

Hydrogels also are provided, which, in embodiments, comprise a first solution comprising an aldehyde component comprising at least one of (i) a first polymer component comprising a first polymer having one or more aldehydes, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol; and a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol.

Also provided are methods for treating, adhering, or sealing biological tissue. In embodiments, the methods comprise providing a first solution comprising an aldehyde component comprising at least one of (i) a first polymer component comprising a first polymer having one or more aldehydes, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol; providing a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol; combining the first and second solutions together to produce a hydrogel; and contacting one or more biological tissues with the hydrogel.

DETAILED DESCRIPTION

Figure 1:
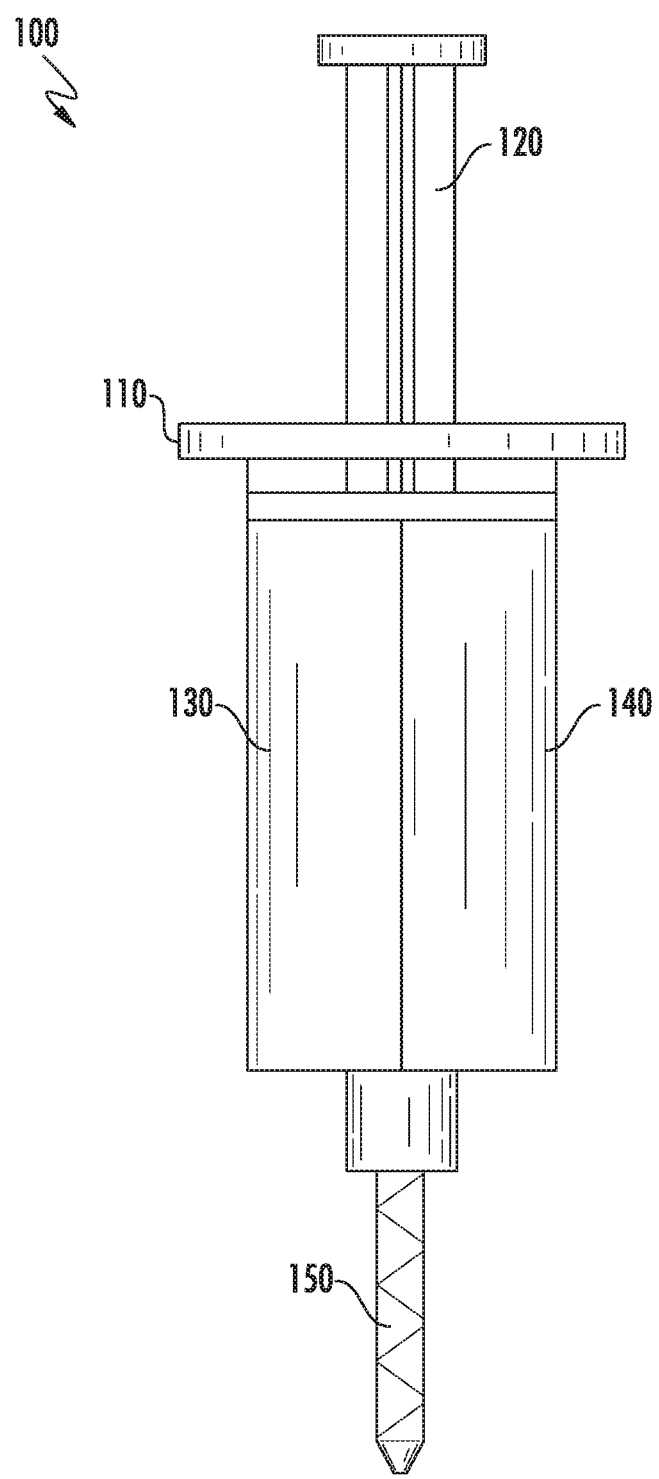
FIG. 1 depicts one embodiment of a kit as described herein.

Provided herein are hydrogels and compositions formed, at least in part, from narrowly distributed multi-arm polyethylene glycol (PEG) compounds.

Improved hydrogels, compositions, such as drug delivery compositions, and methods have been developed for adhering, sealing, or treating one or more biological tissues. Generally, the hydrogels and compositions provided herein are formed from one or more solutions comprising at least one narrowly distributed multi-armed PEG compound.

Generally, in embodiments, the hydrogels and compositions may be used on or in any amine-containing surface or area. For example, the hydrogels and compositions may be used on or in any internal or external biological tissues, lumens, orifices, or cavities. The biological tissues, lumens, orifices, or cavities may be human or other mammalian tissues, lumens, orifices, or cavities. The biological tissues may be natural or artificially generated. Therefore, the biological tissues may be in vivo or in vitro. The biological tissues may be skin, bone, ocular, muscular, vascular, or an internal organ, such as lung, intestine, heart, liver, etc.

In some embodiments, the hydrogels and compositions serve as a matrix material for controlled release of drug. In other embodiments, the hydrogels and compositions may be used in medical applications as a scaffold, filler, prosthetic, artificial tissue, or a combination thereof. The hydrogels and compositions can be applied to a tissue site in a human or other animal patient, for example, during a surgical or other medical procedure. In one embodiment, the hydrogels and compositions are used to create or seal an anastomosis. In particular embodiments, the hydrogels and compositions are used to adhere, seal, and/or treat a wound, lesion, or a combination thereof. For example, the hydrogels and compositions may be applied to slow-healing or troublesome wounds, such as those suffered by diabetics. In one embodiment, the hydrogels and compositions may be used to secure or help secure a medical implant, such as an orthopedic implant, at a selected tissue site within a human or other animal patient.

Hydrogels and Compositions

Generally, the hydrogels and compositions, including drug delivery compositions, provided herein may be formed by combining a first solution and a second solution as described herein. The first solution and the second solution may be aqueous solutions. The first solution and/or the second solution may independently include water, phosphate buffer saline (PBS), Dulbecco's Modified Eagle's Medium (DMEM), or any combination thereof.

The first solution, in embodiments, comprises an aldehyde component. The aldehyde component generally includes a polymeric material with one or more functional groups capable of reacting with one or more functional groups on a biological tissue and/or one or more functional groups on an amine component of a second solution. The aldehyde component, in some embodiments, includes a polymer, such as a polysaccharide, having one or more aldehyde groups. The aldehyde component, in further embodiments, includes a narrowly distributed multi-armed PEG, as described herein, that is substituted with one or more aldehyde groups. In particular embodiments, the aldehyde component includes (i) a polymer, such as a polysaccharide, having one or more aldehyde groups, and (ii) a narrowly distributed multi-armed PEG, as described herein, that is substituted with one or more aldehyde groups.

The second solution generally comprises an amine component. The amine component includes one or more functional groups capable of reacting with the one or more functional groups on the aldehyde component. The amine component may include one or more primary amines, secondary amines, or a combination thereof. The amine component, in embodiments, comprises a narrowly distributed multi-armed PEG, as described herein, that is substituted with one or more amines.

The first solution and the second solution, in embodiments, are combined to form the hydrogels and compositions described herein. When combined, the aldehyde groups of the aldehyde component react with the amines that are present on the amine component. This reaction is referred to herein as "curing" or "gelling."

In embodiments, the concentration of aldehyde component in the first solution is about 0.01% to about 50% by weight of the first solution. In further embodiments, the concentration of aldehyde component in the first solution is about 0.01% to about 30% by weight of the first solution. In some embodiments, the concentration of aldehyde component in the first solution is about 0.01% to about 20% by weight of the first solution. In additional embodiments, the concentration of aldehyde component in the first solution is about 0.01% to about 10% by weight of the first solution. In one embodiment, the concentration of the aldehyde component in the first solution is about 5% by weight of the first solution. In another embodiment, the concentration of the aldehyde component in the first solution is about 10% by weight of the first solution. In yet another embodiment, the concentration of the aldehyde component in the first solution is about 20% by weight of the first solution. Typically, the concentration may be tailored and/or adjusted based on the particular application, tissue type, and/or the type and concentration of the amine component.

In embodiments, the concentration of the aldehyde component in the hydrogels or compositions described herein is about 0.01% to about 20% by weight of the hydrogel or composition. In further embodiments, the concentration of the aldehyde component in the hydrogels or compositions described herein is about 0.01% to about 15% by weight of the hydrogel or composition. In some embodiments, the concentration of the aldehyde component in the hydrogels or compositions described herein is about 0.01% to about 10% by weight of the hydrogel or composition. In still further embodiments, the concentration of the aldehyde component in the hydrogels or compositions described herein is about 0.01% to about 7% by weight of the hydrogel or composition.

In embodiments, the concentration of amine component in the second solution is about 0.01% to about 50% by weight of the second solution. In further embodiments, the concentration of amine component in the second solution is about 10% to about 40% by weight of the second solution. In some embodiments, the concentration of amine component in the second solution is about 20% to about 40% by weight of the second solution. In additional embodiments, the concentration of amine component in the second solution is about 30% to about 40% by weight of the second solution. In one embodiment, the concentration of amine component in the second solution is about 15% by weight of the second solution. In another embodiment, the concentration of amine component in the second solution is about 30% by weight of the second solution. In a further embodiment, the concentration of amine component in the second solution is about 35% by weight of the second solution. In a still further embodiment, the concentration of amine component in the second solution is about 40% by weight of the second solution. Typically, the concentration may be tailored and/or adjusted based on the particular application, tissue type, and/or the type and concentration of aldehyde component.

In embodiments, the concentration of amine component in the hydrogels or compositions described herein is about 0.01% to about 30% by weight of the hydrogel or composition. In further embodiments, the concentration of amine component in the hydrogels or compositions described herein is about 0.01% to about 25% by weight of the hydrogel or composition. In some embodiments, the concentration of amine component in the hydrogels or compositions described herein is about 0.01% to about 15% by weight of the hydrogel or composition. In still further embodiments, the concentration of amine component in the hydrogels or compositions described herein is about 0.01% to about 10% by weight of the hydrogel or composition.

In embodiments, the concentration of aldehyde component in the first solution is about 0.01% to about 50% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In further embodiments, the concentration of aldehyde component in the first solution is about 0.01% to about 30% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In some embodiments, the concentration of aldehyde component in the first solution is about 0.01% to about 20% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In additional embodiments, the concentration of aldehyde component in the first solution is about 0.01% to about 10% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In one embodiment, the concentration of the aldehyde component in the first solution is about 5% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In another embodiment, the concentration of the aldehyde component in the first solution is about 10% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution. In yet another embodiment, the concentration of the aldehyde component in the first solution is about 20% by weight of the first solution, and the concentration of amine component in the second solution is about 0.01% to about 50% by weight of the second solution, about 10% to about 40% by weight of the second solution, about 20% to about 40% by weight of the second solution, about 30% to about 40% by weight of the second solution, about 15% by weight of the second solution, about 30% by weight of the second solution, about 35% by weight of the second solution, or about 40% by weight of the second solution.

In embodiments, the concentration of amine component in the second solution is about 0.01% to about 50% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In further embodiments, the concentration of amine component in the second solution is about 10% to about 40% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In some embodiments, the concentration of amine component in the second solution is about 20% to about 40% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In additional embodiments, the concentration of amine component in the second solution is about 30% to about 40% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In one embodiment, the concentration of amine component in the second solution is about 15% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In another embodiment, the concentration of amine component in the second solution is about 30% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In a further embodiment, the concentration of amine component in the second solution is about 35% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution. In a still further embodiment, the concentration of amine component in the second solution is about 40% by weight of the second solution, and the concentration of aldehyde component in the first solution is about 0.01% to about 50% by weight of the first solution, about 0.01% to about 30% by weight of the first solution, about 0.01% to about 20% by weight of the first solution, about 0.01% to about 10% by weight of the first solution, about 5% by weight of the first solution, about 10% by weight of the first solution, or about 20% by weight of the first solution.

Narrowly Distributed Multi-armed PEG Compounds

In embodiments, the aldehyde component comprises at least one narrowly distributed multi-armed PEG compound. In other embodiments, the amine component comprises at least one narrowly distributed multi-armed PEG compound. In further embodiments, the aldehyde component and the amine component comprise at least one narrowly distributed multi-armed PEG compound.

The phrase "narrowly distributed multi-armed PEG," as used herein, refers to a polymer component having a polymer backbone comprising at least two alkylene portions that independently include 2 to 8 adjacent carbon atoms that are substituted with polyethylene glycol having a functional group, such as an aldehyde or amine. The functional group of the polyethylene glycol may be a terminal functional group. The at least two alkylene portions may be separated from each other by a spacer portion of the polymer backbone. The spacer portion may comprise an alkylene, arylene, cycloalkylene, or a combination thereof that is not substituted with polyethylene glycol. The alkylene, arylene, and cycloalkylene of the spacer portion may be independently substituted or unsubstituted, as described herein. For example, the alkylene, arylene, and/or cycloalkylene, as described herein, may independently include an ether moiety in their structures. When the spacer portion is selected from a combination of an alkylene, arylene, and/or cycloalkylene, the selected groups may have an ether bond connecting at least two of the selected groups. For example, the spacer portion may include an aryloxyalkylene group.

In embodiments, the narrowly distributed multi-armed PEG compounds provided herein have the following structure:

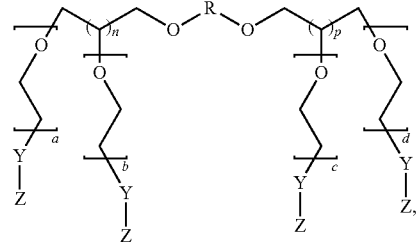

Formula (I)

wherein n is 1 to 6, p is 1 to 6, a is 3 to 600, b is 3 to 600, c is 3 to 600, d is 3 to 600, R is a group selected from, substituted or unsubstituted, alkylene, arylene, cycloalkylene, or a combination thereof, Y is a single bond or an alkylene group, and Z is an aldehyde or amine. The alkylene, arylene, and/or cycloalkylene, as described herein, may independently include an ether moiety in their structures. When R is selected from a combination of an alkylene, arylene, and/or cycloalkylene, the selected groups may have an ether bond connecting at least two of the selected groups. For example, "R" may include an aryloxyalkylene group.

In embodiments, the narrowly distributed multi-armed PEG compounds have a structure according to Formula (I), wherein R is an unsubstituted alkylene having 4 carbon atoms, n is 3, p is 3, Y is a single bond, and a, b, c, and d are at least substantially equal to each other. The phrase "a, b, c, and d are at least substantially equal to each other" may be satisfied, for example, when a, b, c, and d of at least one molecule of Formula (II) are equal to each other, or the average of a, b, c, and d of a plurality of molecules of Formula (II) are equal to each other or substantially equal to each other, such as within 10% of each other. In these embodiments, the narrowly distributed multi-armed PEG compounds have the following structure:

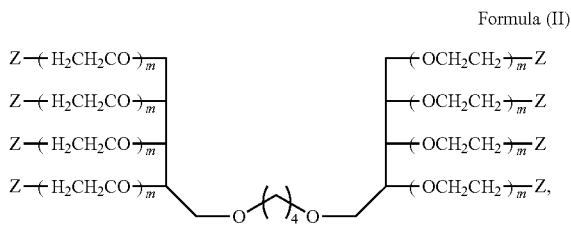

Formula (II)

wherein m is 3 to 600, and Z is an aldehyde or amine. In one embodiment, m is 5 to 300. In a further embodiment, m is 13 to 250. In a still further embodiment, m is 13 to 50.

In embodiments, the narrowly distributed multi-armed PEG compounds have a structure according to Formula (I), wherein R is an unsubstituted alkylene having 4 carbon atoms, n is 3, p is 3, and a, b, c, and d are at least substantially equal to each other. In these embodiments, the narrowly distributed multi-armed PEG compounds have the following structure:

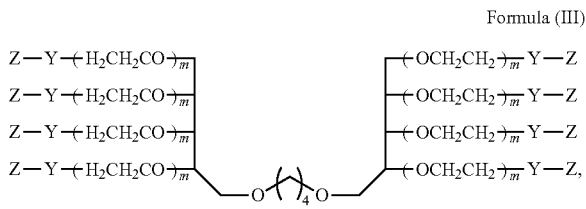

Formula (III)

wherein m is 3 to 600, Y is a single bond or an alkylene group, and Z is an aldehyde or amine. In one embodiment, m is 5 to 300. In a further embodiment, m is 13 to 250. In a still further embodiments, m is 13 to 50.

As used herein, the term "alkylene" refers to linear or branched hydrocarbyl groups of 1 to 12 carbon atoms that may be substituted or unsubstituted. The alkylene groups described herein may include 3 to 8 carbon atoms. In a particular embodiment, the alkylene groups include 4 carbon atoms. Non-limiting examples of alkylene groups include an ethylene group, a propylene group, an isopropylene group, an n-butylene group, an s-butylene group, a t-butylene group, a pentamethylene group, a hexamethylene group, a heptamethylene group, an octamethylene group, a nonamethylene group, a decamethylene group, an undecamethylene group, a dodecamethylene group, and the like. In further embodiments, the alkylene groups include at least one ether moiety. An ether moiety may be arranged between two carbon atoms of an alkylene. For example, an alkylene may be an alkyleneoxyalkylene. An ether moiety also may be arranged at the end of an alkylene. In still further embodiments, the alkylene includes one or more of the following moieties (which may be arranged between two carbon atoms of the alkylene or at its end): an ether, an ester, a urethane, an amide, a carbonate, a secondary amino group, a urea, a thioether, and/or a thioester.

The term "arylene," as used herein, includes a substituted or unsubstituted arylene having 6 to 12 carbon atoms. Non-limiting examples of arylene groups include a phenylene group, a naphthylene group, an anthrylene group, and the like. The arylene groups herein may include an ether moiety. The ether moiety may be arranged between two carbons of an arylene, or may include one carbon of an arylene and one carbon of another part of a chemical compound or structure.

The term "cycloalkylene," as used herein, includes a substituted or unsubstituted cycloalkylene having 5 to 12 carbon atoms. Non-limiting examples of cycloalkylene groups include a cyclopentylene group, a cyclohexylene group, a cycloheptylene group, a cyclooctylene group, a cyclononylene group, a cyclodecylene group, and the like. The cycloalkylene groups herein may include an ether moiety. The ether moiety may be arranged between two carbons of a cycloalkylene, or may include one carbon of an cycloalkylene and one carbon of another part of a chemical compound or structure.

The term "amine" or "amine group," as used herein, refers to primary amines, such as —$NH_2$, secondary amines, such as —NHR—, or a combination thereof, and groups of atoms that include an amine. The term "aldehyde" or "aldehyde group," as used herein, refers to aldehydes or groups of atoms that include an aldehyde. The amines and aldehydes described herein may include one or more atoms that permit the amine or aldehyde, respectively, to be bonded to the chemical structures. The one or more atoms may have been included in an amine-containing or aldehyde-containing starting material used to make the compositions herein. For example, the amine may include an oxygen atom, and have the following structure: —$ONH_2$.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

Aldehyde Component

The first solution described herein includes an aldehyde component. The aldehyde component, in one embodiment, is a narrowly distributed multi-armed PEG having one or more aldehydes. The aldehyde component, in another embodiment, is a first polymer component comprising a first polymer, such as a polysaccharide, having one or more aldehydes. The aldehyde component, in a further embodiment, comprises (i) a first polymer component comprising a first polymer, such as a polysaccharide, having one or more aldehydes, and (ii) a narrowly distributed multi-armed PEG having one or more aldehydes.

1. Narrowly Distributed Multi-arm PEG Aldehydes

In embodiments, the aldehyde component includes a narrowly distributed multi-arm PEG aldehyde, which is a polymer component having a polymer backbone comprising at least two alkylene portions that independently include 2 to 8 adjacent carbon atoms that are substituted with polyethylene glycol having a terminal aldehyde group, wherein the at least two alkylene portions are separated from each other by a first spacer portion of the polymer backbone, the first spacer portion comprising an alkylene, arylene, cycloalkylene, or a combination thereof that is not substituted with polyethylene glycol.

In one embodiment, the aldehyde component comprises a compound having the structure of Formula (I), wherein Z is an aldehyde, and the other variables are as defined previously herein. In another embodiment, the aldehyde component comprises a compound having the structure of Formula (II), wherein Z is an aldehyde, and m is 3 to 600. In a further embodiment, the aldehyde component comprises a compound having the structure of Formula (II), wherein Z is an aldehyde, and m is 5 to 300. In yet another embodiment, the aldehyde component comprises a compound having the structure of Formula (II), wherein Z is an aldehyde, and m is 13 to 250. In an additional embodiment, the aldehyde component comprises a compound having the structure of Formula (II), wherein Z is an aldehyde, and m is 13 to 50.

In another embodiment, the aldehyde component comprises a compound having the structure of Formula (III), wherein Z is an aldehyde, and m is 3 to 600. In a further embodiment, the aldehyde component comprises a compound having the structure of Formula (III), wherein Z is an aldehyde, and m is 5 to 300. In yet another embodiment, the aldehyde component comprises a compound having the structure of Formula (III), wherein Z is an aldehyde, and m is 13 to 250. In an additional embodiment, the aldehyde component comprises a compound having the structure of Formula (III), wherein Z is an aldehyde, and m is 13 to 50.

In embodiments, the aldehyde component comprises a compound having the structure of Formula (III), wherein Z is an aldehyde, Y is —$CH_2$—, and m is 3 to 600. In other embodiments, the aldehyde component comprises a compound having the structure of Formula (III), wherein Z is an aldehyde, Y is —$CH_2$—, and m is 5 to 300. In particular embodiments, the aldehyde component comprises a compound having the structure of Formula (III), wherein Z is an aldehyde, Y is —$CH_2$—, and m is 13 to 250. In certain embodiments, the aldehyde component comprises a compound having the structure of Formula (III), wherein Z is an aldehyde, Y is —$CH_2$—, and m is 13 to 50.

2. First Polymer Component

Generally, the first polymer component comprises a polymer with one or more functional groups capable of reacting with one or more functional groups on a biological tissue and/or one or more functional groups on the amine component. In embodiments, the one or more functional groups comprise aldehydes. Therefore, the first polymer component may comprise a first polymer having one or more aldehydes.

In certain embodiments, the first polymer is at least one polysaccharide. In these embodiments, the at least one polysaccharide may be linear, branched, or have both linear and branched sections within its structure. Generally, the at least one polysaccharide may be natural, synthetic, or modified—for example, by cross-linking, altering the polysaccharide's substituents, or both. In one embodiment, the at least one polysaccharide is plant-based. In another embodiment, the at least one polysaccharide is animal-based. In yet another embodiment, the at least one polysaccharide is a combination of plant-based and animal-based polysaccharides. Non-limiting examples of polysaccharides include, but are not limited to, dextran, chitin, starch, agar, cellulose, hyaluronic acid, or a combination thereof.

In certain embodiments, the first polymer has a molecular weight of about 1,000 to about 1,000,000 Daltons. In one embodiment, the first polymer has a molecular weight of about 5,000 to about 15,000 Daltons. Unless specified otherwise, the "molecular weight" of the polymer refers to the number average molecular weight.

In some embodiments, the first polymer is functionalized so that its structure includes one or more functional groups that will react with one or more functional groups on a biological tissue and/or one or more functional groups on the amine component. In one embodiment, the one or more functional groups incorporated into the first polymer's structure includes an aldehyde.

In certain embodiments, the first polymer's degree of functionalization is adjustable. The "degree of functionalization" generally refers to the number or percentage of reactive groups on the first polymer that are replaced or converted to the desired one or more functional groups. In one embodiment, the degree of functionalization is adjusted based on the type of tissue to which the hydrogel or composition is applied, the concentration(s) of the components, and/or the type of amine component used to form the hydrogels or compositions. In one embodiment, the degree of functionalization is about 10% to about 75%. In another embodiment, the degree of functionalization is about 15% to about 50%. In yet another embodiment, the degree of functionalization is about 20% to about 30%.

In one embodiment, the first polymer is dextran with a molecular weight of about 10 kDa. In another embodiment, the first polymer is dextran having about 50% of its hydroxyl group converted to aldehydes. In a further embodiment, the first polymer is dextran with a molecular weight of about 10 kDa and about 50% of its hydroxyl groups converted to aldehydes.

In some embodiments, a polysaccharide is oxidized to include a desired percentage of one or more aldehyde functional groups. Generally, this oxidation may be conducted using any known means. For example, suitable oxidizing agents include, but are not limited to, periodates, hypochlorites, ozone, peroxides, hydroperoxides, persulfates, and percarbonates. In one embodiment, the oxidation is performed using sodium periodate. Typically, different amounts of oxidizing agents may be used to alter the degree of functionalization.

In addition to the above-described aldehyde component, the first solution may also comprise one or more additives. In one embodiment, the additive is compatible with the aldehyde component. In another embodiment, the additive does not contain primary or secondary amines. Generally, the amount of additive varies depending on the application, tissue type, concentration of the first solution, the type of aldehyde component, the type of amine component, and the concentration of the second solution. Examples of suitable additives, include, but are not limited to, pH modifiers, stabilizers, thickeners, antimicrobial agents, colorants, surfactants, and radio-opaque compounds. In other embodiments, the first solution comprises a foaming agent.

In embodiments, the additive is a stabilizer. The stabilizer, in particular embodiments, may be one that prevents or reduces protein adsorption, especially after deployment. In one embodiment, the stabilizer is MPC copolymer. In some embodiments, the first solution comprises MPC copolymer in an amount of about 0.01% to about 10% by weight of the first solution. For example, the first solution may comprise MPC copolymer in an amount of about 5% by weight of the first solution. In further embodiments, the second solution comprises MPC copolymer in an amount of about 0.01% to about 10% by weight of the second solution. For example, the second solution may comprise MPC copolymer in an amount of about 5% by weight of the second solution. In particular embodiments, the first solution and second solution comprise MPC copolymer, independently, in an amount of about 0.01% to about 10% by weight of the first solution and second solution, respectively. As used herein, "MPC" or "MPC copolymer" refers to a polymer including 2-methacryloyloxy ethyl phosphorylcholine; for example, a copolymer of 2-methacryloyloxy ethyl phosphorylcholine and acrylate or methacrylate monomer having a side chain substituted by one or more amines.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water.

In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the first solution and/or aldehyde component comprises at least one drug. In such embodiments, the hydrogels or compositions may serve as a matrix material for controlled release of drug. The drug may be essentially any drug suitable for local, regional, or systemic administration from a quantity of the hydrogel or composition that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. Other drugs are envisioned.

In other particular embodiments, the first solution and/or aldehyde component comprises one or more cells. For example, the hydrogels or compositions may serve as a matrix material for delivering cells to a tissue site at which the hydrogel or composition has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Amine Component

The second solution generally comprises an amine component. The amine component, in embodiments, is a narrowly distributed multi-armed PEG amine having a polymer backbone comprising at least two alkylene portions of 2 to 8 adjacent carbon atoms that are substituted with polyethylene glycol having a terminal amine group, wherein the at least two alkylene portions are separated from each other by a spacer portion of the polymer backbone, the spacer portion comprising at least two carbon atoms that are not substituted with polyethylene glycol.

In one embodiment, the amine component comprises a compound having the structure of Formula (I), wherein Z is an amine, and the other variables are as defined previously herein. In another embodiment, the amine component comprises a compound having the structure of Formula (II), wherein Z is an amine, and m is 3 to 600. In a further embodiment, the amine component comprises a compound having the structure of Formula (II), wherein Z is an amine, and m is 5 to 300. In yet another embodiment, the amine component comprises a compound having the structure of Formula (II), wherein Z is an amine, and m is 13 to 250. In an additional embodiment, the amine component comprises a compound having the structure of Formula (II), wherein Z is an amine, and m is 13 to 50.

In another embodiment, the amine component comprises a compound having the structure of Formula (III), wherein Z is an amine, and m is 3 to 600. In a further embodiment, the amine component comprises a compound having the structure of Formula (III), wherein Z is an amine, and m is 5 to 300. In yet another embodiment, the amine component comprises a compound having the structure of Formula (III), wherein Z is an amine, and m is 13 to 250. In an additional embodiment, the amine component comprises a compound having the structure of Formula (III), wherein Z is an amine, and m is 13 to 50.

In embodiments, the amine component comprises a compound having the structure of Formula (III), wherein Z is an amine, Y is —$CH_2$—, and m is 3 to 600. In some embodiments, the amine component comprises a compound having the structure of Formula (III), wherein Z is an amine, Y is —$CH_2$—, and m is 5 to 300. In still further embodiments, the amine component comprises a compound having the structure of Formula (III), wherein Z is an amine, Y is —$CH_2$—, and m is 13 to 250. In additional embodiments, the amine component comprises a compound having the structure of Formula (III), wherein Z is an amine, Y is —$CH_2$—, and m is 13 to 50.

In addition to the above-described amine component, the second solution may also comprise one or more additives. In one embodiment, the additive is compatible with the amine component. In another embodiment, the additive does not contain aldehydes. Generally, the amount of additive varies depending on the application, tissue type, concentration of the first solution, the type of aldehyde component, the type of amine component, and the concentration of the second solution. Examples of suitable additives, include, but are not limited to, pH modifiers, thickeners, antimicrobial agents, colorants, surfactants, and radio-opaque compounds. In other embodiments, the second solution comprises a foaming agent.

In embodiments, the additive is a stabilizer. In one embodiment, the stabilizer is MPC copolymer.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water.

In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the second solution and/or amine component comprises at least one drug. In such embodiments, the hydrogels or compositions may serve as a matrix material for controlled release of drug. The drug may be essentially any drug suitable for local, regional, or systemic administration from a quantity of the hydrogel or composition that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. Other drugs are envisioned.

In other particular embodiments, the second solution and/or amine component comprises one or more cells. For example, the hydrogels or compositions may serve as a matrix material for delivering cells to a tissue site at which the hydrogel or composition has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Formation of Hydrogels and Compositions

Generally, the hydrogels and compositions described herein may be formed by combining the first solution and the second solution in any manner. In some embodiments, the first solution, and the second solution are combined before contacting a biological tissue. In other embodiments, the first solution, and the second solution are combined, in any order, on or in a biological tissue. In further embodiments, the first solution is applied to a first biological tissue, the second solution is applied to a second biological tissue, and the first and second biological tissues are contacted. In still a further embodiment, the first solution is applied to a first region of a biological tissue, the second solution is applied to a second region of a biological tissue, and the first and second regions are contacted.

Generally, the hydrogels and compositions may be applied to one or more biological tissues as an adhesive, sealant, and/or treatment. The one or more biological tissues may be diseased, damaged (e.g., dissected), healthy, or some combination thereof. In one embodiment, the hydrogels and compositions are applied to one or more biological tissues as an adhesive. In another embodiment, the hydrogels and compositions are applied to one or more biological tissues as a sealant. In a further embodiment, the hydrogels and compositions are applied to one or more biological tissues as a treatment. In an additional embodiment, the hydrogels and compositions are applied to one or more biological tissues as an adhesive and sealant. In still another embodiment, the hydrogels and compositions are applied to one or more biological tissues as an adhesive and treatment. In yet another embodiment, the hydrogels and compositions are applied to one or more biological tissues as a sealant and treatment. In a still further embodiment, the hydrogels and compositions are applied to one or more biological tissues as an adhesive, sealant, and treatment.

The hydrogels and compositions may be applied to the biological tissue using any suitable tool and methods. Non-limiting examples include the use of syringes or spatulas. Double barrel syringes with rigid or flexible discharge tips, and optional extension tubes, known in the art are envisioned.

As used herein, the hydrogels and compositions are a "treatment" when they improve the response of at least one biological tissue to which they are applied. In some embodiments, the improved response is lessening overall inflammation, improving the specific response at the wound site/interface of the tissue and hydrogels or compositions, enhancing healing, repairing torn or broken tissue, or a combination thereof. As used herein, the phrase "lessening overall inflammation" refers to an improvement of histology scores that reflect the severity of inflammation. As used herein, the phrase "improving the specific response at the wound site/interface of the tissue and hydrogels or compositions" refers to an improvement of histology scores that reflect the severity of serosal neutrophils. As used herein, the phrase "enhancing healing" refers to an improvement of histology scores that reflect the severity of serosal fibrosis.

In embodiments, the hydrogels and compositions provided herein are used as tissue adhesives, tissue sealants, tissue treatments, matrix materials, fillers, coatings, or a combination thereof. In some embodiments, the hydrogels and compositions are used in tissue engineering applications, including orthopedic applications, which require demanding mechanical characteristics during implantation and tissue regeneration. In other embodiments, the hydrogels and compositions are used at least as part of a procedure for repairing focal cartilage defects, and/or as an osteoinductive/osteocondutive "putty" for bone repair or spinal fusion. In additional embodiments, the hydrogels and compositions may be used in a variety of structural roles, including those that require a high strength adhesive and/or a coating. In still further embodiments, hydrogels and compositions can be used as a bioactive adhesive coating for drug delivery applications.

In embodiments, the hydrogels and compositions may be used for localized drug delivery. The drugs that may be delivered with the hydrogels and compositions include, but are not limited to small molecule drugs, biologics, or a combination thereof.

In embodiments, the hydrogels and compositions may be used as a degradable scaffold for tissue engineering applications. The hydrogels and compositions may assist with guiding the infiltration and differentiation of cells to repair a tissue defect.

In embodiments, the hydrogels and compositions may be used in challenging or awkward implantation environments, including under flowing liquids and/or in inverted geometries.

Before or after contacting one or more biological tissues, the hydrogels and compositions may be allowed adequate time to cure or gel. When the hydrogels and compositions "cure" or "gel," as those terms are used herein, it means that the one or more functional groups of the aldehyde component have undergone one or more reactions with the amine component, and one or more biological tissues. Not wishing to be bound by any particular theory, it is believed that the hydrogels and compositions described herein are effective because the aldehyde component reacts with both (i) the amine component, and (ii) the surface of the biological tissues. In certain embodiments, the aldehyde functional groups of the aldehyde component react with the amines on (i) the amine component, and (ii) the biological tissues to form imine bonds. In these embodiments, it is believed that the amines of the amine component react with a high percentage of the aldehydes of the aldehyde component, thereby reducing toxicity and increasing biocompatibility of the hydrogels and compositions. Typically, the time needed to cure or gel the hydrogels and compositions will vary based on a number of factors, including, but not limited to, the characteristics of the aldehyde component, amine component, the concentrations of the first solution and second solution, and the characteristics of the one or more biological tissues. In embodiments, the hydrogels and compositions will cure sufficiently to provide desired bonding or sealing shortly after the components are combined. The gelation or cure time should provide that a mixture of the components can be delivered in fluid form to a target area before becoming too viscous or solidified and then once applied to the target area sets up rapidly thereafter. In one embodiment, the gelation or cure time is less than 120 seconds. In another embodiment, the gelation or cure time is between 3 and 60 seconds. In a particular embodiment, the gelation or cure time is between 5 and 30 seconds.

In certain embodiments, one or more foaming agents are added to the first solution and/or second solution before the solutions are combined. In one embodiment, the foaming agents comprise a two part liquid system comprising Part 1 and Part 2, wherein Part 1 comprises a bicarbonate and Part 2 comprises an aqueous solution of di- or polyaldehydes and a titrant. A wide range of di- or polyaldehydes exist, and their usefulness is restricted largely by availability and by their solubility in water. For example, aqueous glyoxal (ethanedial) is useful, as is aqueous glutaraldehyde (pentadial). Water soluble mixtures of di- and polyaldehydes prepared by oxidative cleavage of appropriate carbohydrates with periodate, ozone or the like may also be useful.

A titrant is most preferably employed in the liquid solution of Part 2. More specifically, the titrant is an organic or inorganic acid, buffer, salt, or salt solution which is capable of reacting with the bicarbonate component of Part 1 to generate carbon dioxide and water as reaction by-products. The carbon dioxide gas that is generated creates a foam-like structure of the hydrogels and compositions and also causes the volume of the hydrogels and compositions to expand.

Most preferably, the titrant is an inorganic or organic acid that is present in an amount to impart an acidic pH to the resulting mixture of the Part 1 and Part 2 components. Preferred acids that may be employed in the practice of the present invention include phosphoric acid, sulfuric acid, hydrochloric acid, acetic acid, and citric acid.

Tissue Specific Formulations

Generally, the hydrogels and compositions may be adjusted in any manner to compensate for differences between tissues. In one embodiment, the amount of aldehyde component is increased or decreased while the amount of amine component is unchanged. In another embodiment, the amount of amine component is increased or decreased while the amount of aldehyde component is unchanged. In another embodiment, the concentration of the aldehyde component in the first solution is increased or decreased while the second solution is unchanged. In yet another embodiment, the concentration of the amine component in the second solution is increased or decreased while the first solution is unchanged. In a further embodiment, the concentrations of the both the aldehyde component in the first solution and the amine component in the second solution are changed.

When the amine density on the surface of a particular biological tissue is unknown due to disease, injury, or otherwise, an excess of the first solution may, in some embodiments, be added when the hydrogels and compositions are first applied, then the amount of first solution may be reduced, e.g., incrementally or drastically, until the desired effect is achieved. The "desired effect," in this embodiment, may be an appropriate or adequate curing time, adhesion, sealing, treatment, or a combination thereof. Not wishing to be bound by any particular theory, it is believed that an excess of the first solution may be required, in some instances, to obtain the desired effect when the amine density on a biological tissue is low. Therefore, adding an excess will help the user, in this embodiment, achieve adequate sealing or adhesion or treatment in less time. This is particularly desirable in emergency situations.

In other embodiments, however, a lower amount of the first solution may be added when the hydrogels and compositions are first applied, then the amount of first solution may be increased, e.g., incrementally or drastically, until the desired effect is achieved, which may be adequate curing time, adhesion, sealing, treatment, or a combination thereof.

In embodiments, the hydrogels and compositions can be optimized in view of a target biological tissue, by adjusting one or more of the following: rheology, mechanics, chemistry/adhesion, degradation rate, drug release, and bioactivity. These can be adjusted, in embodiments, by altering the type and/or concentration of amine component, the type and/or concentration of aldehyde component, or a combination thereof.

Hydrogel and Composition Kits

In another aspect, a kit is provided that comprises a first part that includes the first solution, and a second part that includes the second solution. The kit may further include an applicator or other device means, such as a multi-compartment syringe, for storing, combining, and delivering the two solutions and/or the resulting hydrogels and compositions to a tissue site.

In one embodiment, the kit comprises separate reservoirs for the first solution and the second solution. In certain embodiments, the kit comprises reservoirs for first solutions of different concentrations. In other embodiments, the kit comprises reservoirs for second solutions of different concentrations. In further embodiments, the kit comprises reservoirs for first solutions of different concentrations, and reservoirs for second solutions of different concentrations.

In one embodiment, the kit comprises instructions for selecting an appropriate concentration or amount of at least one of the first solution and/or second solution to compensate or account for at least one characteristic of one or more biological tissues. In one embodiment, the hydrogels and compositions are selected based on one or more predetermined tissue characteristics. For example, previous tests, may be performed to determine the number of density of bonding groups on a biological tissue in both healthy and diseased states. Alternatively, a rapid tissue test may be performed to assess the number or density of bonding groups. Quantification of tissue bonding groups can be performed by contacting a tissue with one or more materials that (1) have at least one functional group that specifically interacts with the bonding groups, and (2) can be assessed by way of fluorescence or detachment force required to separate the bonding groups and the material. In another embodiment, when the density of bonding groups on a biological tissue is unknown, an excess of the first polymer having one or more aldehydes, may be initially added as described herein to gauge the density of bonding groups on the surface of the biological tissue.

In certain embodiments, the kit comprises at least one syringe. In one embodiment, the syringe comprises separate reservoirs for the first solution and second solution. The syringe may also comprise a mixing tip that combines the two solutions as the plunger is depressed. The mixing tip may be release-ably securable to the syringe (to enable exchange of mixing tips), and the mixing tip may comprise a static mixer. In some embodiments, the reservoirs in the syringe may have different sizes or accommodate different volumes of solution. In other embodiments, the reservoirs in the syringe may be the same size or accommodate the same volumes of the solution. In a further embodiment, one reservoir may comprise Part 1 of the foaming composition described hereinabove, and a second reservoir may comprise Part 2 of the foaming composition.

FIG. 1 depicts one embodiment of a syringe 100. The syringe 100 includes a body 110 with two reservoirs (130, 140). A first solution is disposed in the first reservoir 130, and a second solution is disposed in the second reservoir 140. The two reservoirs (130, 140) are emptied by depressing the plunger 120, which pushes the contents of the two reservoirs (130, 140) into the mixing tip 150 and out of the syringe 100.

In a further embodiment, one or more of the reservoirs of the syringe may be removable. In this embodiment, the removable reservoir may be replaced with a reservoir containing a first solution or second solution of a desired concentration.

In a preferred embodiment, the kit is sterile. For example, the components of the kit may be packaged together, for example in a tray, pouch, and/or box. The packaged kit may be sterilized using known techniques at suitable wavelengths (where applicable), such as electron beam irradiation, gamma irradiation, ethylene oxide sterilization, or other suitable techniques.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

EXAMPLES

Example 1

Hydrogels Formed with Narrowly Distributed Multi-armed PEGs

A series of hydrogels were made using narrowly distributed multi-armed PEGs.

The narrowly distributed multi-armed PEGs of this particular example had the following generic structure:

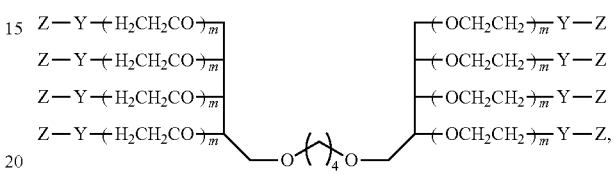

wherein "m" was 28. The compound of this particular example had a polydispersity of about 1.02.

For the aldehyde component of this example, Z was an aldehyde, Y was a single bond, and this particular aldehyde component was referred to as DX-100AL2. For the amine component of this example, Z was a primary amine, Y was —$CH_2$—, and this particular amine component was referred to as DX-100PA.

These particular components were combined to determine whether they would form a hydrogel, or possibly polymerize to form a plastic polymer.

A first solution was prepared that included water and DX-100AL2 in an amount of 10% by weight of the first solution. A second solution was prepared that included water and DX-100PA in an amount of 15% by weight of the second solution. Both of the solutions were filtered after being prepared. The components of each solution also were fluorescently labeled to track their degradation over time.

When the first solution and second solution of this example were combined, a hydrogel formed. The hydrogel, however, degraded within about 1 hour, which was determined with the aid of the fluorescent labels. Quickly degrading hydrogels are useful for certain applications, but more stable hydrogels were formed when the concentration(s) of the first solution and second solution were increased, as explained, for instance, in the following example.

Example 2

Comparison of Conventional and Narrowly Distributed Multi-armed PEGs

The tests of this example demonstrated that increasing the concentrations of DX-100AL2 and DX-100PA resulted in hydrogels having improved stability. The tests also demonstrated that hydrogels made from two narrowly distributed multi-armed PEGs were more stable than those made from one conventional multi-armed PEG and one narrowly distributed multi-arm PEG.

The conventional multi-armed PEG of this example was referred to as HEGO-100AL2, and had the following generic structure:

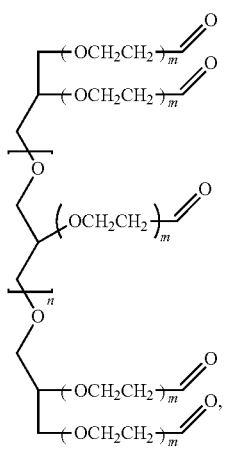

wherein m was 28, and n was 0 to 4. The compound of this particular example had a polydispersity of about 1.10.

This generic structure demonstrated that conventional multi-armed PEG materials had a larger distribution of derivatives compared to the narrowly distributed multi-armed PEG compounds described herein.

Using the procedure described at Example 1, a series a hydrogels were made using various concentrations of DX-100PA, DX-100AL2, and HEGO-100AL2. The following table summarizes the characteristics of each hydrogel made in this example:

| | Amine Component (Percent by Weight of First Solution) | Aldehyde Component (Percent by Weight of Second Solution) | |
|---|---|---|---|
| Sample No. | DX-100PA | DX-100AL2 | HEGO-100AL2 |
| 1 | 30 | 30 | — |
| 2 | 30 | — | 30 |
| 3 | 35 | 35 | — |
| 4 | 35 | — | 35 |
| 5 | 40 | 40 | — |
| 6 | 40 | — | 40 |

Figure 2A:
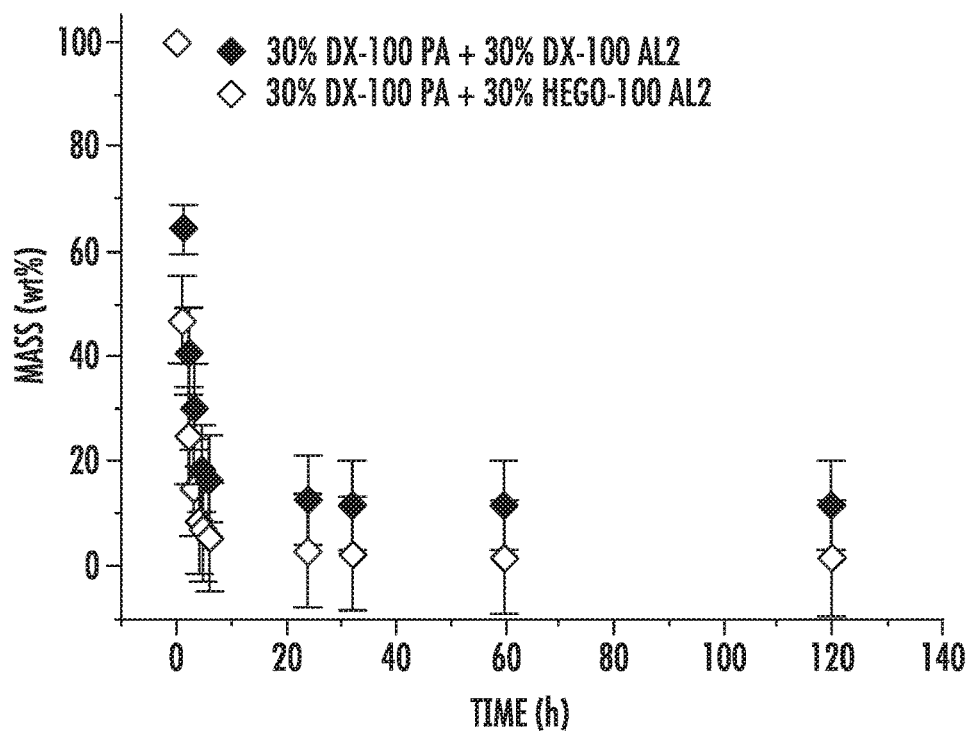
FIG. 2A depicts the stability of several embodiments of hydrogels, which include conventional multi-armed PEGs and narrowly distributed multi-armed PEGs.
Figure 2B:
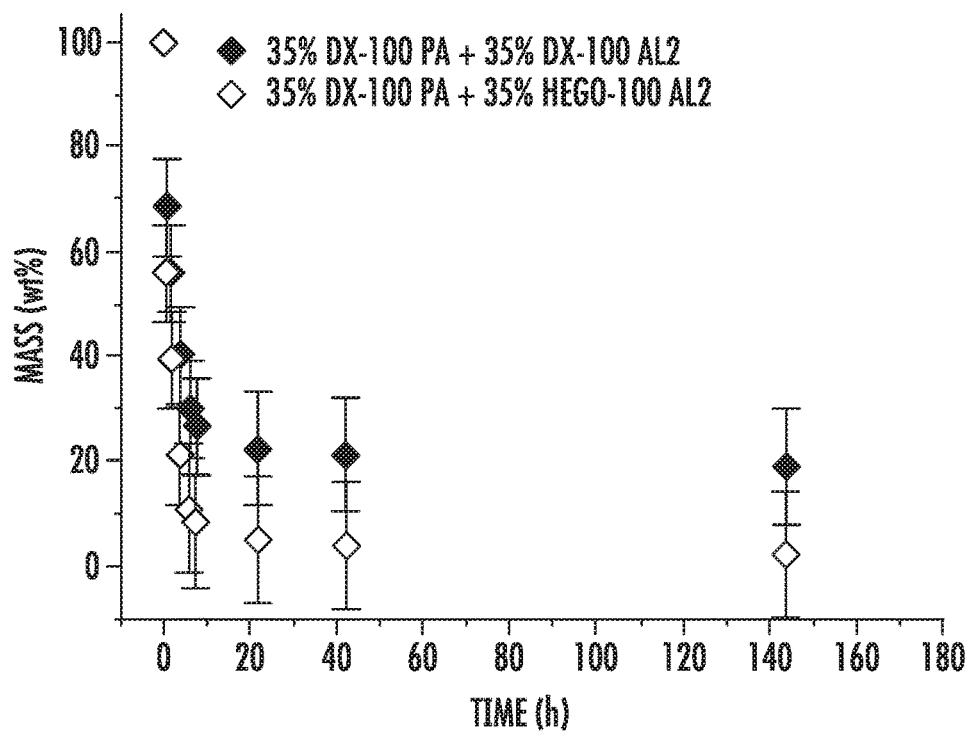
FIG. 2B depicts the stability of several embodiments of hydrogels, which include conventional multi-armed PEGs and narrowly distributed multi-armed PEGs.
Figure 2C:
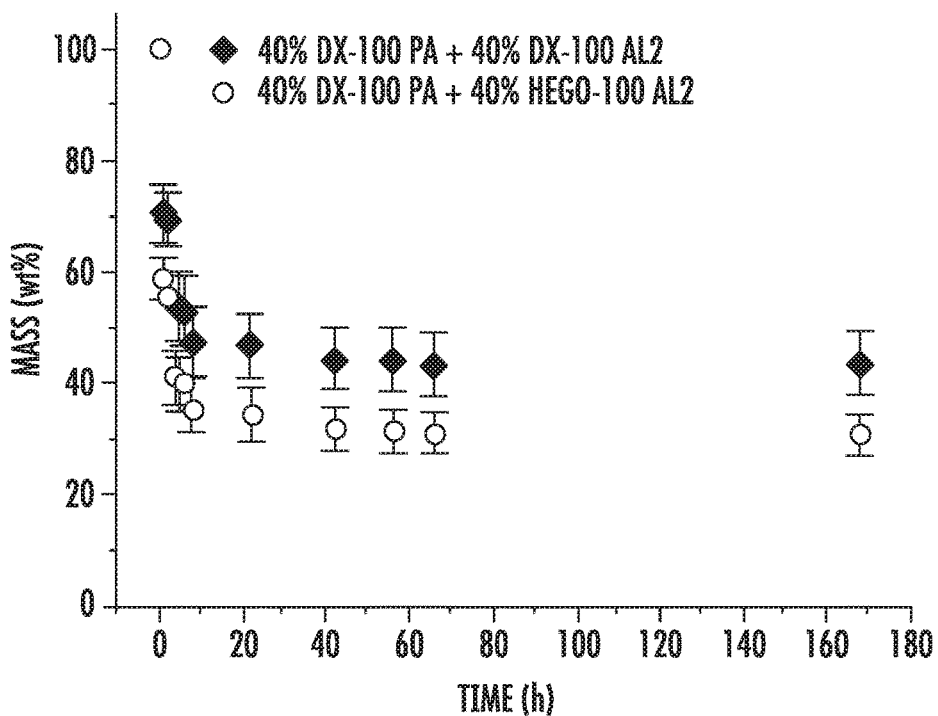
FIG. 2C depicts the stability of several embodiments of hydrogels, which include conventional multi-armed PEGs and narrowly distributed multi-armed PEGs.

The stability of each of samples 1-6 was compared, as shown at FIG. 2A, FIG. 2B, and FIG. 2C, which compare the stabilities of samples 1 and 2, samples 3 and 4, and samples 5 and 6, respectively.

FIG. 2A, FIG. 2B, and FIG. 2C demonstrated that the stability of the hydrogels generally increased as the concentration of the components increased. The figures also demonstrated that the hydrogels that contained HEGO-100AL2, which was a conventional multi-armed PEG, were not as stable as the hydrogels formed with two narrowly distributed multi-armed PEG components. This distinction was observed at all concentrations, and became more pronounced as the concentrations of the components were increased (see FIG. 2C).

Example 3

Hydrogels Including an Aldehyde-substituted Dextran

In this example, hydrogels were formed with a dextran substituted with aldehydes, which was referred to as "Dextran AL."

The Dextran AL of this example was a linear dextran having a molecular weight of 10 kDa. The Dextran AL of this example also had about 50% of its hydroxyl groups oxidized to aldehydes.

Dextran AL was combined, in various proportions, with an amine component formed from either (i) a narrowly distributed multi-armed PEG, or (ii) a conventional multi-armed PEG. The conventional multi-armed PEG of this example was referred to as HEGO-100PA, and had the following generic structure:

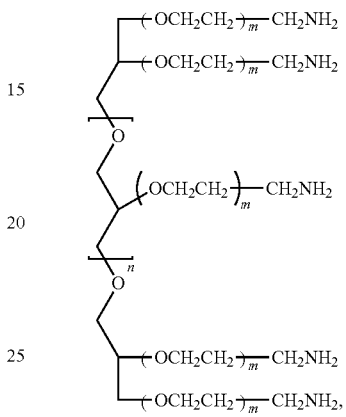

wherein m was 28, and n was 0 to 4. The compound of this particular example had a polydispersity of about 1.10.

To form the hydrogels of this example Dextran AL was combined with either DX-100PA or HEGO-100PA. The hydrogels of this example included the following concentrations:

| | Aldehyde Component (Percent by Weight of Second Solution) | Amine Component (Percent by Weight of First Solution) | |
|---|---|---|---|
| Sample No. | Dextran AL | DX-100PA | HEGO-100PA |
| 1 | 5 | 15 | — |
| 2 | 5 | — | 15 |
| 3 | 10 | 15 | — |
| 4 | 10 | — | 15 |
| 5 | 20 | 15 | — |
| 6 | 20 | — | 15 |

Figure 3A:
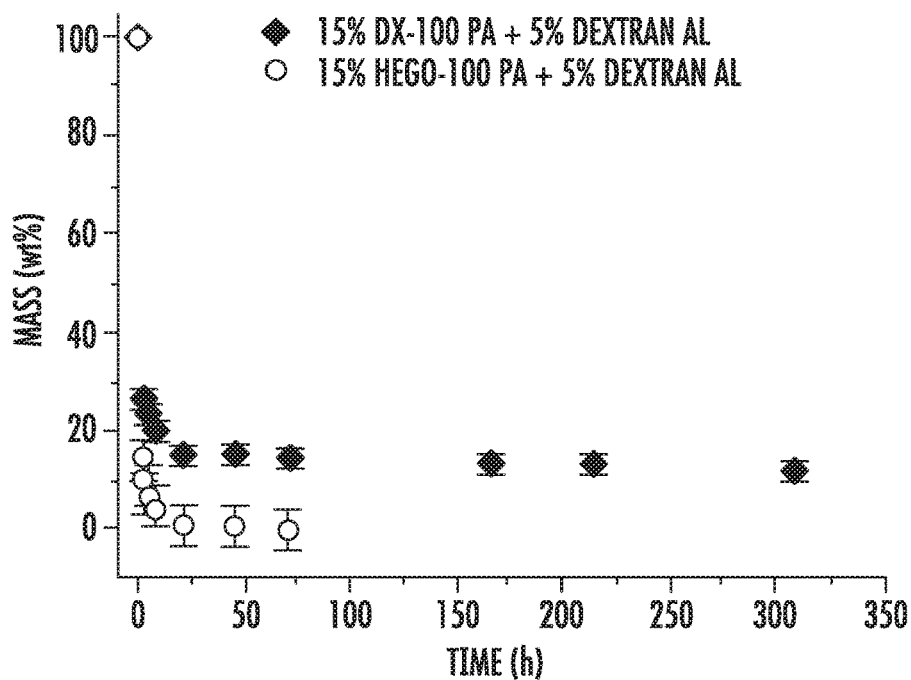
FIG. 3A depicts the stability of several embodiments of hydrogels that include a dextran substituted with aldehydes.
Figure 3B:
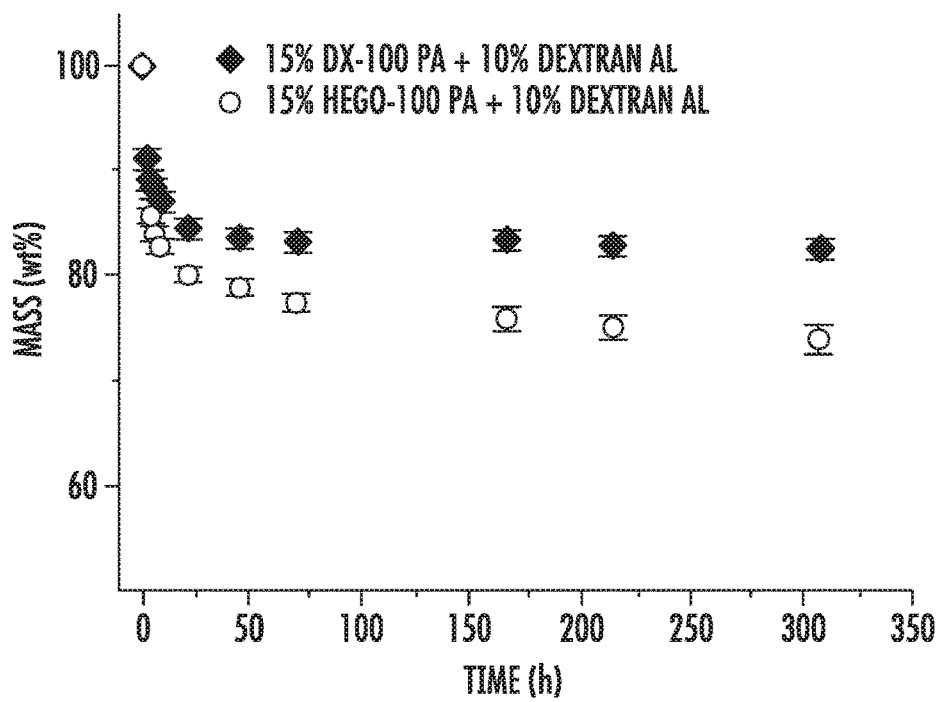
FIG. 3B depicts the stability of several embodiments of hydrogels that include a dextran substituted with aldehydes.
Figure 3C:
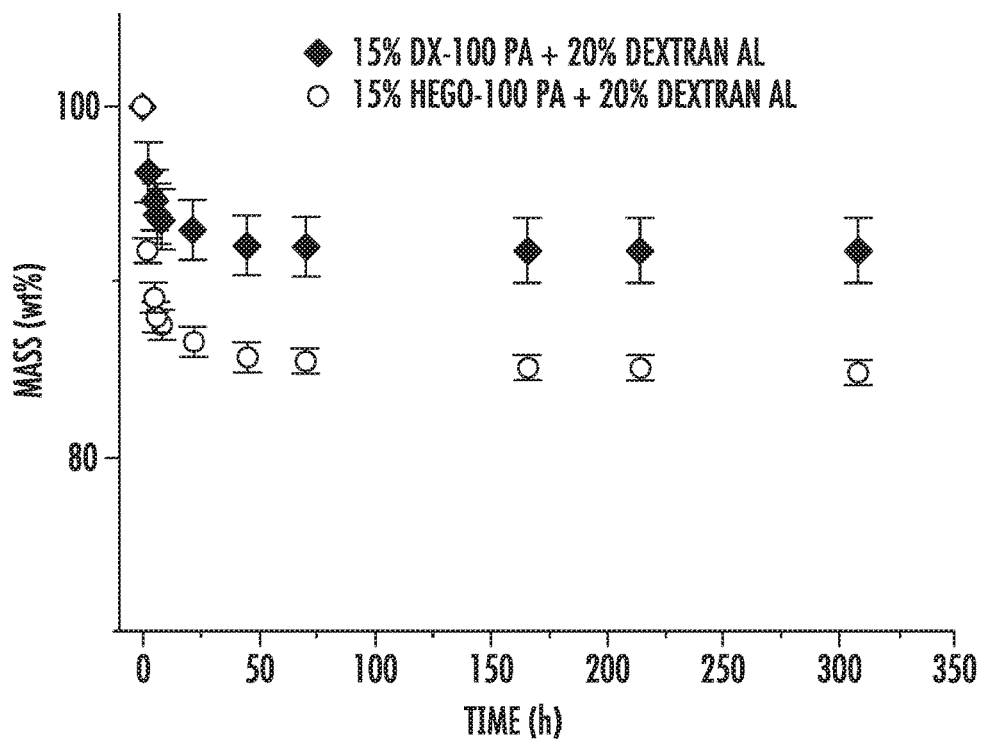
FIG. 3C depicts the stability of several embodiments of hydrogels that include a dextran substituted with aldehydes.

The stabilities of the hydrogels of this table were measured and compared, as shown at FIG. 3A, FIG. 3B, and FIG. 3C, which correspond to samples 1 and 2, samples 3 and 4, and samples 5 and 6, respectively. The data of FIG. 3A, FIG. 3B, and FIG. 3C revealed that the use of Dextran AL generally resulted in stable hydrogels, and that the most stable hydrogels, among those tested, were formed by combining Dextran AL with DX-100PA, which was a narrowly distributed multi-armed PEG substituted with amines. In fact, the stability of the hydrogels formed with DX-100PA increased relative to the stability of the hydrogels formed with HEGO-100PA as the concentration of the amine components were increased (see FIG. 3C).

Example 4

Modulus of Hydrogels

The modulus of a hydrogel containing a conventional multi-armed PEG was compared with the modulus of a hydrogel containing a narrowly distributed multi-armed PEG. Specifically, the modulus of samples 3 and 4 of the table of Example 3 was measured and compared after a two hour incubation in phosphate buffered saline (PBS), as shown at FIG. 4.

Figure 4:
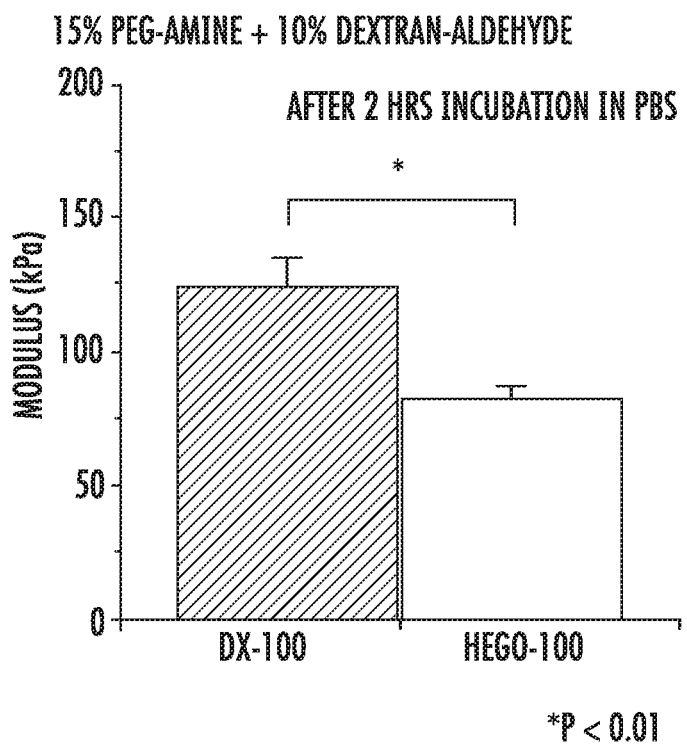
FIG. 4 depicts the modulus of two embodiments of hydrogels.

As shown by FIG. 4, the sample 3 hydrogel, which included a narrowly distributed multi-armed PEG, had a higher modulus than the sample 4 hydrogel, which was made from a conventional multi-armed PEG.

Example 5

Hydrogels Containing an Additive

The effect of an additive to a particular hydrogel was tested in this example. Two hydrogels were made, and included (i) sample 3 of the table of Example 3 without an additive, and (ii) sample 3 of the table of Example 3 with an additive. The additive used in this example was MPC copolymer. MPC copolymer is a water soluble polymer of 2-methacryloyloxy ethyl phosphorylcholine (MPC) and 3-(2-aminoethylsulfanyl)-2-hydroxypropyl 2-methacrylate hydrochloride.

The hydrogel that included MPC copolymer was made by combining a solution that included DX-100PA and MPC copolymer in amounts of 15% and 5%, respectively, by weight of the first solution, and another solution that included DX-100AL2 in an amount of 10% by weight of the other solution.

Figure 5:
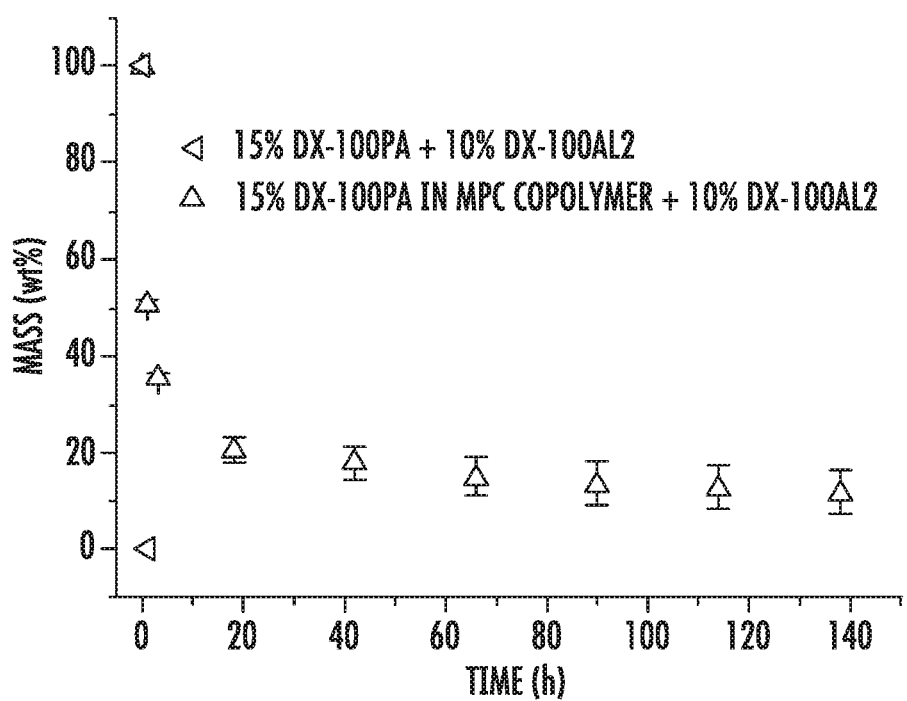
FIG. 5 depicts the stabilities of two embodiments of hydrogels, one of which includes an additive.

The hydrogel that included MPC copolymer was more stable than the hydrogel that did not include MPC copolymer, as shown at FIG. 5.

Example 6

In Vivo Characterization of Hydrogels

Figure 6:
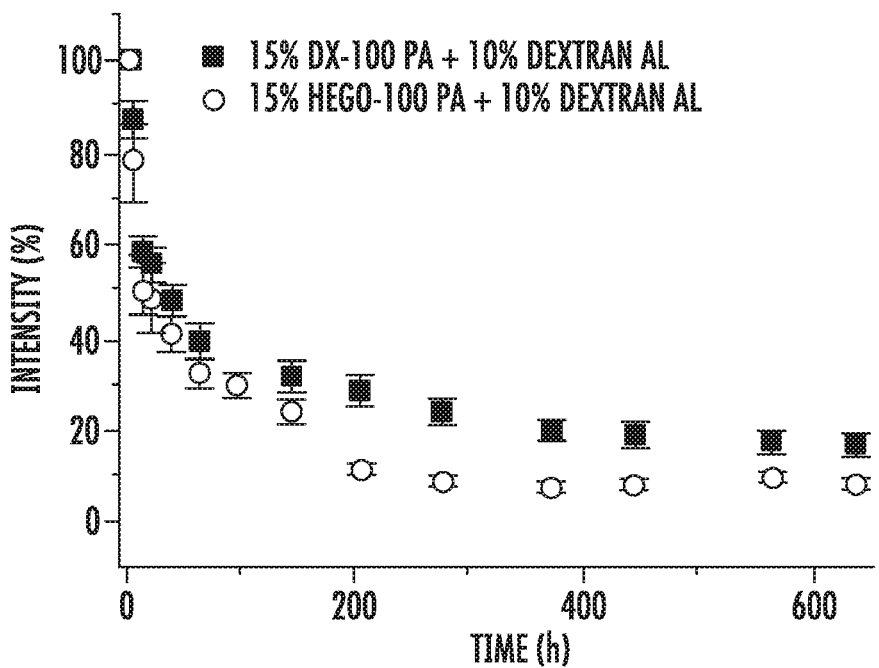
FIG. 6 depicts the in vivo stability of two embodiments of hydrogels.

The stability of various hydrogels were tested in vivo. In the first test that was performed, the in vivo stability of samples 3 and 4 from Example 3 were tested in a series of rats. The intensity of the fluorescent labels was measured at increments from 0 hours to 625 hours, as shown at FIG. 6. These figures demonstrate that the hydrogels that included the narrowly distributed multi-armed PEG amine component were more stable than those formed with a conventional multi-armed PEG amine.

Figure 7:
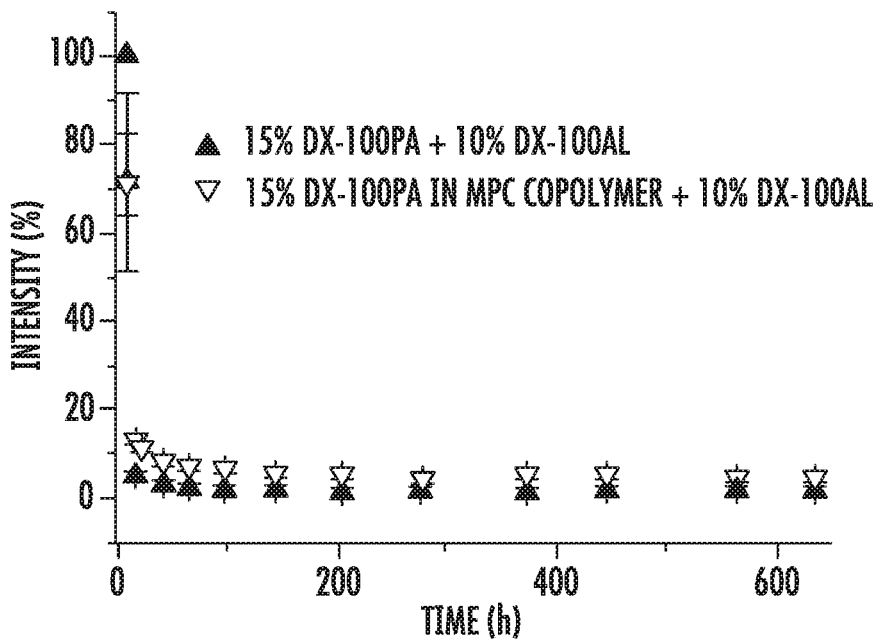
FIG. 7 depicts and compares the in vivo stability of two embodiments of hydrogels, one of which includes MPC copolymer.

Similarly, the in vivo stability of the hydrogels of Example 5 also were tested in a series of rats. FIG. 7 depicts the in vivo stability of a hydrogel formed with DX-100PA and DX-100AL2, and a hydrogel formed with DX-100PA, DX-100AL2, and MPC copolymer. The figures demonstrated that the addition of MPC copolymer generally imparted additional stability to the hydrogel.

We claim:

1. A kit for making a hydrogel, the kit comprising:
a first part that includes a first solution comprising an aldehyde component comprising at least one of (i) a first polymer component comprising a first polymer having one or more aldehydes, wherein the first polymer is a polysaccharide, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol; and
a second part that includes a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol.

2. The kit of claim 1, wherein the first polymer is a dextran.

3. The kit of claim 2, wherein about 50% of the dextran's hydroxyl groups are aldehydes.

4. The kit of claim 1, wherein the first spacer portion and the second spacer portion independently comprise an alkylene, an arylene, a cycloalkylene, or a combination thereof.

5. The kit of claim 4, wherein the alkylene, the arylene, the cycloalkylene, or the combination thereof of the first spacer portion and/or the second spacer portion comprises at least one ether moiety.

6. The kit of claim 1, wherein the second polymer component has the following structure:

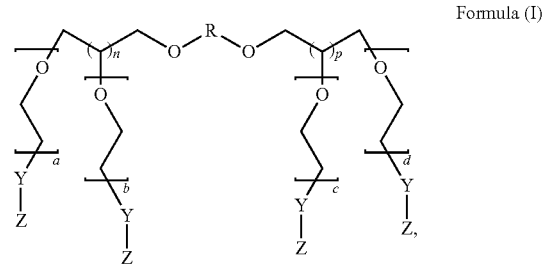

Formula (I)

wherein n is 1 to 6, p is 1 to 6, a is 3 to 600, b is 3 to 600, c is 3 to 600, d is 3 to 600, R is a group selected from alkylene, arylene, cycloalkylene, or a combination thereof, Y is a single bond or an alkylene group, and Z is an aldehyde.

7. The kit of claim 6, wherein R is an unsubstituted alkylene having 4 carbon atoms, n is 3, p is 3, and a, b, c, and d are at least substantially equal to each other, and the second polymer has the following structure:

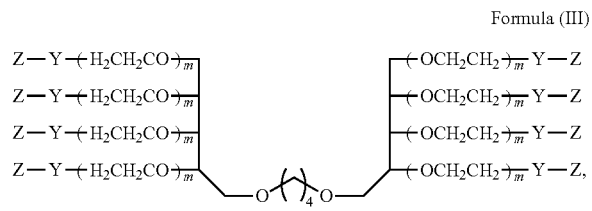

Formula (III)

wherein m is 3 to 600, and Z is an aldehyde.

8. The kit of claim 1, wherein the terminal amine group has the following structure:

—ONH$_2$.

9. The kit of claim 1, wherein the terminal amine group is a primary amine.

10. The kit of claim 1, wherein the amine component has the following structure:

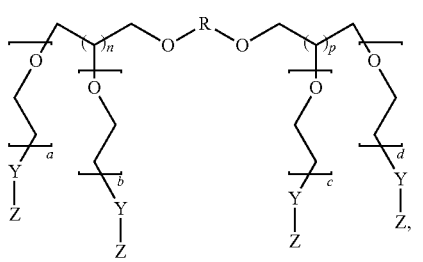

Formula (I)

wherein n is 1 to 6, p is 1 to 6, a is 3 to 600, b is 3 to 600, c is 3 to 600, d is 3 to 600, R is a group selected from alkylene, arylene, cycloalkylene, or a combination thereof, Y is a single bond or an alkylene group, and Z is an amine.

11. The kit of claim 10, wherein R is an unsubstituted alkylene having 4 carbon atoms, n is 3, p is 3, and a, b, c, and d are at least substantially equal to each other, and the amine component has the following structure:

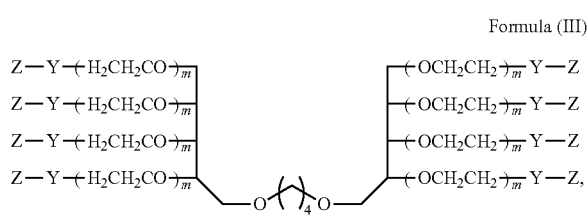

Formula (III)

wherein m is 3 to 600, and Z is an amine.

12. The kit of claim 1, wherein the aldehyde component is present in the first solution in an amount of about 0.01% to about 50% by weight of the first solution.

13. The kit of claim 1, wherein the amine component is present in the second solution in an amount of about 0.01% to about 50% by weight of the second solution.

14. The kit of claim 1, wherein the first solution, the second solution, or both further comprise a 2-methacryloyloxy ethyl phosphorylcholine (MPC) copolymer.

15. The kit of claim 14, wherein the first solution comprises the 2-methacryloyloxy ethyl phosphorylcholine (MPC) copolymer in an amount of about 0.01% to about 10% by weight of the first solution.

16. The kit of claim 14, wherein the second solution comprises the 2-methacryloyloxy ethyl phosphorylcholine (MPC) copolymer in an amount of about 0.01% to about 10% by weight of the second solution.

17. The kit of claim 1, wherein at least one of the first solution and the second solution comprises a drug.

18. The kit of claim 1, wherein at least one of the first solution and the second solution comprises stem cells or other cells.

19. The kit of claim 1, further comprising a syringe, wherein the first solution and the second solution are stored in the syringe.

20. The kit of claim 19, wherein the syringe comprises a mixing tip.

21. A drug delivery composition comprising:
a first solution comprising an aldehyde component comprising at least one of (i) a first polymer component comprising a first polymer having one or more aldehydes, wherein the first polymer is a polysaccharide, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol;
a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol; and
a drug dispersed within the first solution, the second solution, or both the first solution and the second solution.

22. The drug delivery composition of claim 21, wherein the first polymer is a dextran.

23. The drug delivery composition of claim 21, wherein the second polymer has the following structure:

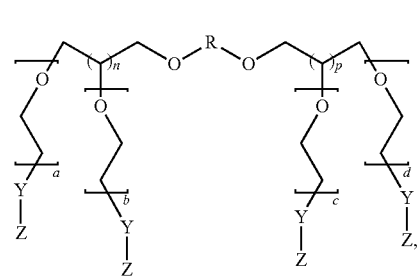

Formula (I)

wherein n is 1 to 6, p is 1 to 6, a is 3 to 600, b is 3 to 600, c is 3 to 600, d is 3 to 600, R is a group selected from alkylene, arylene, cycloalkylene, or a combination thereof, Y is a single bond or an alkylene group, and Z is an aldehyde.

24. The drug delivery composition of claim 21, wherein the amine component has the following structure:

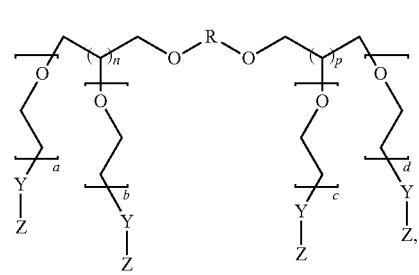

Formula (I)

wherein n is 1 to 6, p is 1 to 6, a is 3 to 600, b is 3 to 600, c is 3 to 600, d is 3 to 600, R is a group selected from alkylene, arylene, cycloalkylene, or a combination thereof, Y is a single bond or an alkylene group, and Z is an amine.

25. A method for local delivery of a drug to a biological tissue, comprising:
   applying to the biological tissue the drug delivery composition of claim 21; and
   permitting the at least one drug to diffuse from the composition into the biological tissue.

26. A method for treating, adhering, or sealing biological tissue, the method comprising:
   providing a first solution comprising an aldehyde component comprising at least one of (i) a first polymer component comprising a first polymer having one or more aldehydes, wherein the first polymer is a polysaccharide, and (ii) a second polymer component having a first polymer backbone comprising at least two first alkylene portions that independently include 2 to 8 adjacent carbon atoms that are substituted with polyethylene glycol having a terminal aldehyde group, wherein the at least two first alkylene portions are separated from each other by a first spacer portion of the first polymer backbone, the first spacer portion comprising at least two carbon atoms that are not substituted with polyethylene glycol;
   providing a second solution comprising an amine component having a second polymer backbone comprising at least two second alkylene portions of 2 to 8 adjacent carbon atoms that are substituted with polyethylene glycol having a terminal amine group, wherein the at least two second alkylene portions are separated from each other by a second spacer portion of the second polymer backbone, the second spacer portion comprising at least two carbon atoms that are not substituted with polyethylene glycol;
   combining the first and second solutions together to produce a hydrogel; and
   contacting one or more biological tissues with the hydrogel.

27. The method of claim 26, wherein the first solution and the second solution are combined in a tip of a syringe.

28. The method of claim 26, wherein the first solution and the second solution are combined on the one or more biological tissues.

29. The method of claim 26, wherein the second solution is applied to the one or more biological tissues followed by the first solution.

30. The method of claim 26, wherein the one or more biological tissues comprise human tissue.

31. The method of claim 26, wherein at least one of the first solution and the second solution comprises a drug.

32. The method of claim 26, wherein at least one of the first solution and the second solution comprises stem cells or other cells.

* * * * *